United States Patent [19]

Sorensen et al.

[11] Patent Number: 4,754,100
[45] Date of Patent: Jun. 28, 1988

[54] CATALYTIC CONVERSION OF $C_3$ ALIPHATICS TO HIGHER HYDROCARBONS

[75] Inventors: Charles M. Sorensen, Wilmington, Del.; Rene B. LaPierre, Medford, N.J.; Roger A. Morrison, Deptford, N.J.; Philip Varghese, Voorhees, N.J.

[73] Assignee: Mobil Oil Corporation, New York, N.Y.

[21] Appl. No.: 82,399

[22] Filed: Aug. 6, 1987

Related U.S. Application Data

[63] Continuation-in-part of Ser. No. 845,284, Mar. 28, 1986, Pat. No. 4,686,316.

[51] Int. Cl.$^4$ ................................................ C07C 6/10
[52] U.S. Cl. .................................. 585/708; 585/415; 585/640; 585/417
[58] Field of Search ................ 585/415, 708, 640, 417

[56] References Cited

U.S. PATENT DOCUMENTS

| | | | |
|---|---|---|---|
| 3,760,024 | 9/1973 | Cattanach | 585/415 |
| 3,775,501 | 11/1973 | Kaeding et al. | 585/415 |
| 3,845,150 | 10/1974 | Yan et al. | 585/415 |
| 3,960,978 | 6/1976 | Givens et al. | 585/415 |
| 4,070,411 | 1/1978 | Butter et al. | 585/415 |
| 4,180,689 | 12/1979 | Davies et al. | 585/415 |
| 4,288,645 | 9/1981 | Wagstaff | 585/415 |
| 4,291,182 | 9/1981 | Dautzenberg et al. | 585/415 |
| 4,354,049 | 10/1982 | Ball et al. | 585/415 |
| 4,565,897 | 1/1986 | Gane et al. | 585/415 |
| 4,579,987 | 4/1986 | Chang et al. | 585/415 |
| 4,686,316 | 8/1987 | Morrison | 585/415 |

OTHER PUBLICATIONS

Engelen et al, Applied Catalysis, 19, 153–163 (1985).

*Primary Examiner*—Asok Pal
*Attorney, Agent, or Firm*—Alexander J. McKillop; Michael G. Gilman; Lowell G. Wise

[57] ABSTRACT

An improved process is described for converting propane to more valuable hydrocarbons such as butanes and $C_5+$ aliphatics over an acidic catalyst having the structure of ZSM-5 by adding a mono-olefin to the propane feed.

23 Claims, 6 Drawing Sheets

COMPARISON OF PROPANE AND PROPANE/PROPYLENE FEEDS

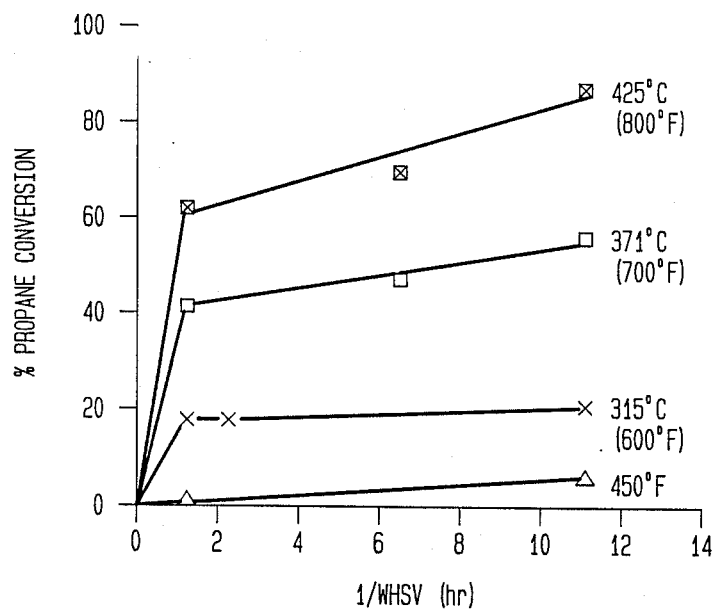

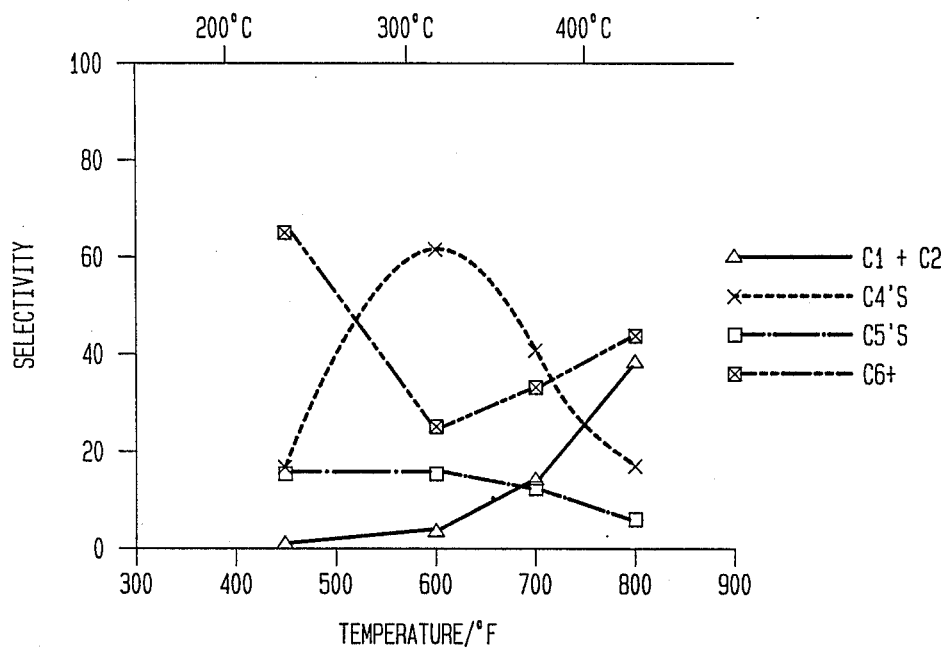

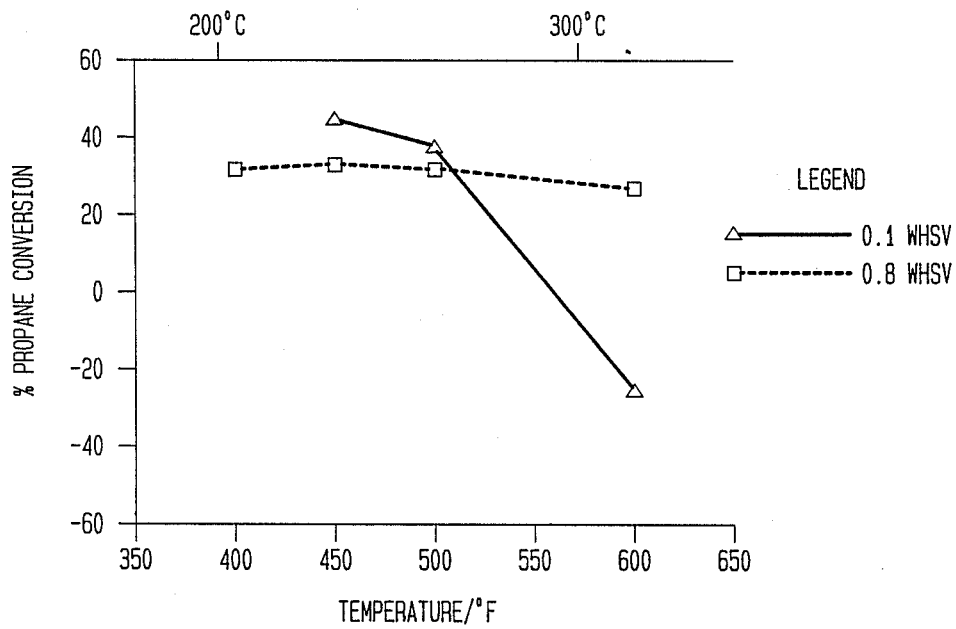

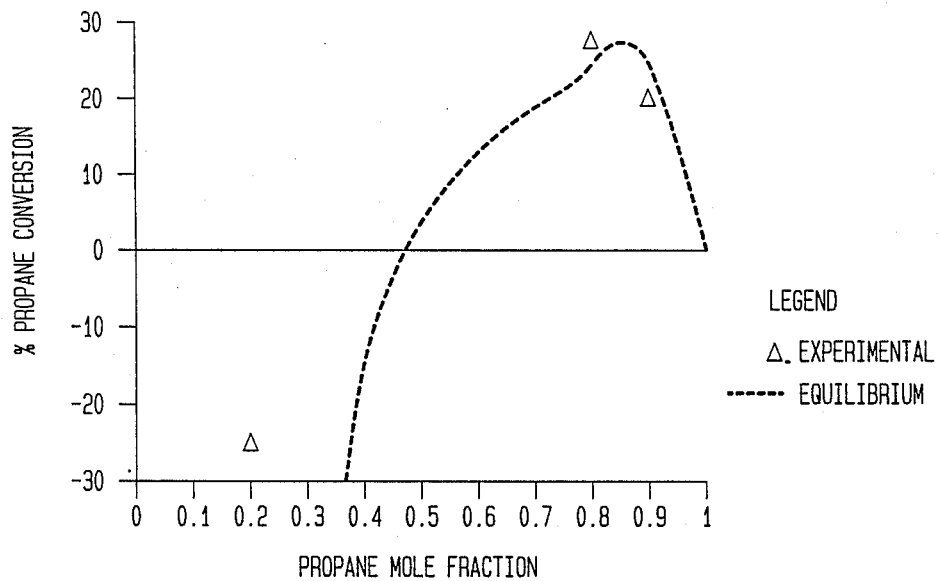

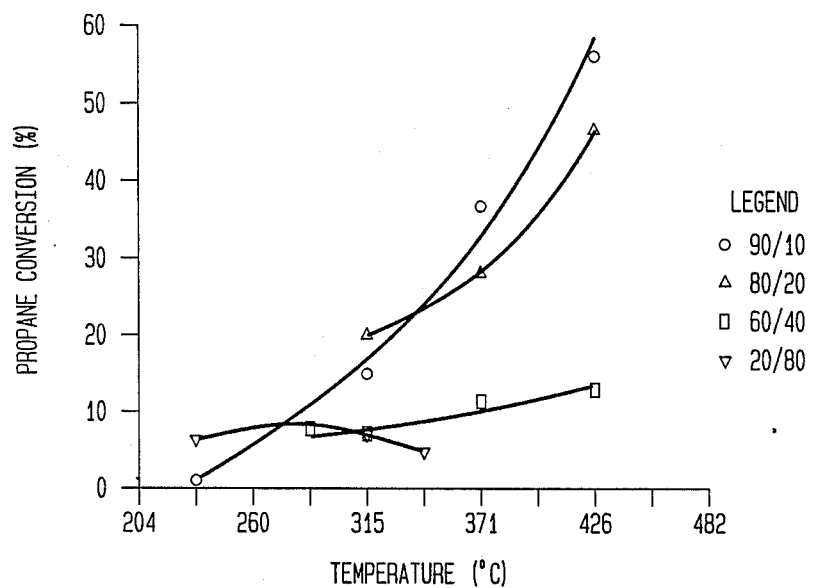

CATALYTIC CONVERSION OF C₃ ALIPHATICS TO HIGHER HYDROCARBONS

REFERENCE TO COPENDING APPLICATION

This application is a continuation-in-part of U.S. patent application Ser. No. 845,284, filed Mar. 28, 1986, now U.S. Pat. No. 4,686,316, incorporated herein by reference.

FIELD OF THE INVENTION

The invention relates to a catalytic process for the production of butanes and $C_5+$ aliphatic hydrocarbons from propane. In particular, it relates to a technique for improving reaction rate for propane feedstock to catalytically convert the feedstock, over an acidic medium pore zeolite.

BACKGROUND OF THE INVENTION

Propane, which is a naturally occurring material and by-product of many petroleum refining processes, has a low economic value and is often burned as a fuel gas or used as a component in liquefied petroleum gas (LPG). Efforts have been made to upgrade propane to move valuable hydrocarbons such as butanes, higher aliphatics, iso-alkanes and aromatics. The isobutane product is a valuable material for the alkylation of lower molecular weight olefins to product gasoline boiling range hydrocarbons. The aromatics product and normal butane can be blended into gasoline to enhance octane rating or can be employed as a petrochemical feedstock.

The prior art suggests a number of methods and process conditions for upgrading a propane feedstock. Many of these methods provide for a mixture of propane and an olefin as feedstock for a catalytic conversion process.

U.S. Pat. No. 3,775,501 (Kaeding, et al.) discloses a process for improving the yield of aromatics from a hydrocarbon such as propane (claim 21) with a crystalline aluminosilicate zeolite catalyst. There is no evidence that a mixed feed of propane and an olefin is employed. The reaction is conducted at temperatures of about 260° C. to 700° C.

U.S. Pat. No. 3,845,150 (Yan, et al.) discloses a process for preparing aromatic hydrocarbons over a ZSM-5 type catalyst from a mixed feed containing about 20%–65% by weight saturates and about 20%–50% by weight olefins. The saturates may comprise a $C_3$ hydrocarbon, and the olefins may comprise propylene. The mixed feed allows for the process to be conducted in a substantially heat balanced condition. There is no disclosure as to the thickness reactivity of the saturated hydrocarbon portion of the feed because of the presence of added olefin. Also, the liquid product resulting from the process comprises substantially insignificant amounts of butanes, and almost all aromatics (e.g., 90% aromatics in Example II).

U.S. Pat. No. 3,960,978 (Givens, et al.) discloses a process for the preparation of a liquid hydrocarbon product comprising predominantly higher olefins and no more than about 20% by weight aromatics, the process employing a mixed feed of $C_1$–$C_5$ paraffins with $C_2$–$C_5$ olefins and a ZSM-5 type catalyst having an alpha value of from about 0.1 to about 120. The yield of butanes from the process is negligible.

SUMMARY OF THE INVENTION

It has now been discovered that propane, when mixed with a controlled amount of mono-olefin, is effectively converted with unexpectedly high selectively to a mixture rich in normal butane, isobutane, pentanes and $C_6+$ aliphatics by contact under a specific set of operating conditions with certain intermediate pore size acid zeolites. In particular, this invention provides a process for the production of $C_4+$ hydrocarbons from a mixture of propane and an amount of lower molecular weight mono-olefin sufficient to increase reaction rate for propane. The preferred process comprises contacting, preferably in the absence of added hydrogen and at a pressure above about 3400 kPa, a feed consisting essentially of propane and a mono-olefin with a catalyst comprising a crystalline alumino-silicate zeolite having a silica-to-alumina ratio of at least 12 and a Constraint Index of 1 to 12, the process reaction being conducted under a combination of conditions of temperature, pressure, and space velocity effective to convert at least 10% of the propane to a mixture of hydrocarbons that contain butanes in an amount equal to at least 35 wt. % of the converted propane.

The total effluent from the catalytic reactor contains unreacted propane, which may be separated and recycled to the fixed bed reaction zone in an amount sufficient to maintain the mixed feed composition to about 60% to 90% propane. The effluent separation step provides a heavier hydrocarbon product containing $C_4+$ aliphatic hydrocarbons, from which an isobutane fraction may be obtained that is useful for conversion to alkylate blending stock for gasoline. Also a normal butane fraction is obtained for gasoline blending. Only a minor amount of $C_1$–$C_2$ hydrocarbons are formed.

In effect, the process of this invention also provides the petroleum refiner with a method for converting propane by-product, which has a low economic value and is often burned for fuel, to much more valuable high-octane alkylate for blending in gasoline. The process of this invention is advantageous is that it requires a very simple process configuration.

Propane can be fed continuously in admixture with a controlled amount of $C_2$–$C_{16}$ mono-olefin, preferably a $C_2$–$C_4$ olefin such as propylene, may be charged continuously to the reactor. The catalyst bed may be a simple fixed bed, although a fluidized bed may be used. Long cycle life is indicated, so that frequent catalyst regeneration is not needed.

DESCRIPTION OF THE DRAWINGS

FIG. 2 is a graph of the effect of temperature on the conversion of propane when the mixed feed of FIG. 1 is employed.

FIG. 3 is a graph of the product selectivity as a function of reaction temperature when the mixed feed of FIG. 1 is employed.

FIG. 4 is a graph of the amount of propane converted as a function of reaction temperature when a 20/80 $C_3$/$C_3$=mixed feed is employed.

FIG. 5 is a graph of both the predicted equilibrium conversions and the experimental results for a propane/propylene mixed feed.

FIG. 6 is a graph of the absolute amount of propane converted (in percent) versus the temperature of the conversion reaction for four different propane/propylene mixed feeds.

DETAILED DESCRIPTION OF THE INVENTION

Figure 1:
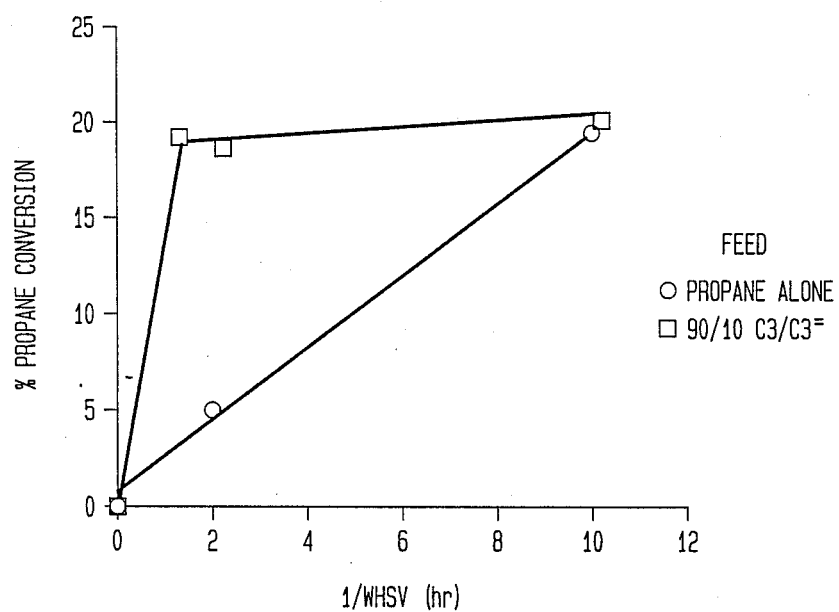
FIG. 1 is a comparison of a pure propane feed and a propane (90 wt. %)/propylene (10 wt. %) mixed feed in a propane conversion reaction.

An improved process had been discovered for converting $C_3$ aliphatic hydrocarbon feed to produce primarily $C_4^+$ aliphatic hydrocarbons by contacting a $C_3$ feed containing propane and about 10% to 40% by weight mono-olefin with an acidic ZSM-5 type zeolite catalyst under reaction conditions to convert at least a portion of the propane. The product recovered is rich in $C_4^+$ aliphatic hydrocarbons such as butane, isobutane, and pentane and contains only a minor amount of methane and ethane. In this description, metric units and parts by weight are employed unless otherwise stated.

The feed to the process of this invention consists essentially of a hydrocarbon mixture having an amount of propane. Suitable sources for the propane feed include petroleum refinery streams such as the $C_3$ cut from FCC off gas, and wet natural gas.

The mono-olefin co-feed includes one or more $C_2$-$C_{16}$ unsaturated hydrocarbons. In a preferred embodiment, the mono-olefin is a $C_2$-$C_4$ hydrocarbon, and, most preferably, propylene. The site of ethylenic unsaturation in the aliphatic molecule can be internal or terminal. Under reaction conditions, the $C_2$-$C_{16}$ olefins will interconvert to give a similar range of hydrocarbon unsaturates.

It has been found that the beneficial effects of olefin addition to the propane feedstock are optimized in defined region of operating conditions. In a preferred embodiment, the mixed feed comprises about 80 wt. % propane and 20 wt. % propylene when the temperature is about 285° C. to 370° C. and the pressure is greater than about 2020 kPa. Although added hydrogen is preferably excluded from the reaction, the feed can be mixed with inert diluents such as nitrogen.

The preferred process minimizes the formation of methane and ethane. In a typical fixed bed reaction under elevated temperature and pressure conversion conditions, a mixed feed comprising about 60 wt. % to 90 wt. % propane and a lower molecular weight mono-olefin or olefin precursor is contacted with a porous crystalline acidic metallosilicate zeolite catalyst having a Constraint Index of 1 to 12 and having an acid cracking activity (alpha value) greater than 100 to convert at least 10 wt. % of the propane to produce hydrocarbons containing not more than 10 wt. % $C_1$-$C_2$ light products, such as methane and/or ethane.

The process may be optimized at a pressure of at least about 800 kPa employing a catalyst comprising a crystalline zeolite having a silica-to-alumina ratio of at least 12 and a Constraint Index of 1 to 2 under a combination of conditions of temperature, pressure, and space velocity (WHSV) effective to convert about 10% to 45% by weight of the propane feed, the improvement of the present process comprises adding to the propane feed sufficient $C_2$-$C_{16}$ mono-olefin to increase the reaction rate of the propane feed; and obtaining a product comprising at least 50% by weight butanes and no more than 10% by weight total methane and ethane, based on conversion of the propane alone.

Rather than adding a $C_2$-$C_{16}$ mono-olefin to the propane, an alternative is to incorporate an olefin precursor into the feedstock. Examples of olefin precursors, which will generate the desired olfins in-situ under reaction conditions, are oxygenated hydrocarbons, such as methanol or other $C_1$-$C_4$ hetero-substituted organic compounds.

Developments in zeolite technology have provided a group of medium pore siliceous materials having similar pore geometry. Most prominent among these intermediate pore size zeolites in ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The metallosilicate catalysts useful in the process of this invention may contain a siliceous zeolite generally known as a shape-selective ZSM-5 type. The members of the class of zeolites useful for such catalysts have an effective pore size of generally from about 5 to about 8 Angstroms such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present invention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 Angstroms. On the other hand, zeolites which provide relatively free access to the internal zeolite structure have a low value for the Constraint Index, and usually have pores of large size, e.g. greater than 8 Angstroms. The method by which Constraint Index is determined is described fully in U.S. Pat. No. 4,016,218, (Haag et al) incorporated herein by reference for details of the method. It is noted that the Constraint Index is determined with the hydrogen form of the zeolite, but that the property is believed to be an attribute of the crystal structure.

Constraint Index (CI) values for some typical materials are shown in Table 1.

TABLE 1

| Zeolite | CI | (at test temperature) |
| --- | --- | --- |
| ZSM-5 | 6–8.3 | (371° C.–316° C.) |
| ZSM-11 | 5–8.7 | (371° C.–316° C.) |
| ZSM-12 | 2.3 | (316° C.) |

TABLE 1-continued

| Zeolite | CI | (at test temperature) |
| --- | --- | --- |
| ZSM-20 | 0.5 | (371° C.) |
| ZSM-22 | 7.3 | (427° C.) |
| ZSM-23 | 9.1 | (427° C.) |
| ZSM-35 | 4.5 | (454° C.) |
| ZSM-38 | 2 | (510° C.) |
| ZSM-48 | 3.5 | (538° C.) |
| ZSM-50 | 2.1 | (427° C.) |
| TMA Offretite | 3.7 | (316° C.) |
| Zeolite Beta | 0.6–2.0 | (316° C.–399° C.) |

The above-described Constraint Index is an important and even critical definition of those ZSM-5 type zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

The class of highly siliceous zeolites defined herein is exemplified by ZSM-5, ZSM-11, ZSM-12, ZSM-22, ZSM-23, ZSM-35, ZSM-38, ZSM-48, and other similar materials. ZSM-5 is described in U.S. Pat. No. 3,702,886 (Argauer et al). ZSM-11 is described in U.S. Pat. No. 3,709,979 (Chu). ZSM-12 is described in U.S. Pat. No. 3,832,449 (Rosinski et al). ZSM-22 is described in U.S. Pat. No. 4,046,859 (Plank et al). ZSM-23 is described in U.S. Pat. No. 4,076,842 (Plank et al). ZSM-35 is described in U.S. Pat. No. 4,016,245 (Plank et al). ZSM-38 is described in U.S. Pat. No. 4,046,859 (Plank et al). ZSM-48 is described in U.S. Pat. No. 4,397,827 (Chu). In a preferred example the catalyst of the present invention comprises aluminosilicate H-ZSM-5 zeolite.

It is desirable in this invention to employ variants of the zeolite that have at least a moderate amount of Bronsted acid activity. A zeolite having a lower silica-to-alumina ratio (e.g. 20:1 to 100:1) is usually preferred since the acid cracking activity as measured by alpha value of the former is higher, typically about 100 to 500. The alpha test, which provides a measure of the relative rate constant of the zeolite for cracking normal hexane (i.e. the alpha value), is described by Miale et al. in Journal of Catalysis, Volume 6, No. 2, October 1966, and is herein incorporated by reference as if fully set forth.

The zeolite component of the catalyst may be the sole component, i.e. it may be shaped into pellets using known methods, and in such shaped form it can serve as an effective catalyst in the process of this invention. The zeolite may be composited with a binder, such as for example with alumina, to form catalyst particles by extrusion or other methods known in the art. Extrudate particles containing about 65 wt. % zeolite and 35 wt. % alumina binder exemplify a catalyst suitable for use in the process of the present invention.

Although the process of the invention can be practiced in the absence of a hydrogenation component, is some instances the presence of such component induces an increase in activity and/or selectivity. Platinum metal acts in such fashion. Other metals which can facilitate hydrogenation-dehydrogenation or olefin disporportionation, such as the Fe or Pt metals of Group VIII of the Periodic Table (IUPAC), metals of Group IIb, titanium, vanadium, chromium, molybdenum, tungsten, rhenium and gallium, may be useful.

For purposes of this invention, the catalytic conversion is effected under a combination of conditions of feed composition (propane/olefin ratio), temperature, pressure, and weight hourly space velocity (WHSV) effective to convert at least 10 wt. % of the propane feed, and effective to provide a selectivity to $C_4^+$ aliphatic hydrocarbons of at least 35 wt %, preferably in the range of about 45 to about 95 wt %. The remainder is converted principally to $C_6^+$ aromatic hydrocarbon, as illustrated hereinafter by example. Since many combinations of feed composition, temperature, pressure, and WHSV will produce conversion and selectivity within the desired range, it is evident that under such conditions it becomes difficult to specify with any simplicity operable ranges for the four individual parameters that are independent of one another. Preferably, the reaction is conducted at a temperature of about 200° C. to 400° C., and most preferably about 200° C. to 370° C., a pressure above about 2850 kPa, a weight hourly space velocity of about 0.1 to 5, a feed composition having a propane:olefin ratio of about 1.5:1 to 9:1, and in the essential absence of added hydrogen. Within the described constraints, useful yields of $C_4^+$ aliphatic hydrocarbons per pass are achieved without encountering rapid aging of the catalyst.

The present invention includes the step of fractionating the hydrocarbon product to obtain isobutane, a $C_3$–$C_4$ hydrocarbon stream rich is unreacted propane, a $C_2^-$ hydrocarbon stream, and a $C_5^+$ hydrocarbon stream. The unconverted propane can be separated and recycled to a fixed bed reaction zone which is packed with HZSM-5 catalyst.

In a preferred embodiment, the process comprises contacting in a fixed bed reaction zone under conversion conditions a mixed feed comprising propane and a mono-olefin or olefin precursor with a porous crystalline acidic metallosilicate zeolite catalyst having a Constraint Index of 1 to 12 and having an acid cracking activity (alpha value) greater than 100, to convert at least 20 wt. % of the propane; withdrawing from the reaction zone a hydrocarbon product containing not more than 10 wt. % cracking products consisting of methane and ethane, and separating a hydrocarbon stream consisting essentially of unreacted propane from the hydrocarbon product and recycling the stream to the fixed bed reaction zone in an amount sufficient to maintain the mixed feed composition at about 60 wt. % to 90 wt. % propane. In an improvement over the prior art, the novel feature of the present process, which results in increased yields of valuable $C_4^+$ aliphatic hydrocarbons such as butanes and pentanes, comprises separating the product to obtain a first fraction consisting essentially of unreacted propane and a second fraction comprising $C_4^+$ aliphatic and aromatic hydrocarbons; recycling the propane-rich first fraction for admixture with the olefin-rich hydrocarbon feedstream to maintain a composite feedstream comprising about 60–90 wt. % propane and about 10–40 wt. % propylene; and conducting the composite feedstream to the reaction zone for catalytic conversion.

It is an object of this invention to produce valuable hydrocarbons, such as butanes and pentanes, and to limit the formation of such undesirable by-products as methane and ethane. In a preferred embodiment, the product contains at least 10% $C_4{}^+$ aliphatic hydrocarbons. The cracking of propane to methane and ethane is kept to a minimum, preferably not more than 10% by weight of the final product, in the present process. This is achieved by adjusting the reaction parameters, including feed composition.

Also, it is an object of this invention to limit the production of aromatic hydrocarbons and to obtain a higher yield of $C_4{}^+$ aliphatic hydrocarbons than was formerly achieved. Preferably, the liquid product of the fixed bed catalytic reaction contains no more than 40 wt. % aromatics.

FIG. 1 illustrates a comparison of essentially pure propane and a 9:1 mixture of propane and propene when employed as feedstocks in a catalytic conversion reaction of the present invention. Co-feeding propylene with propane increases the propane conversion rate, especially at short space time (1/WHSV). The increased reactivity of propane, caused by the presence of limited amounts of added olefin, permits high propane conversion at higher space velocities than those achieved when propane alone is converted. High space velocity operation results in greater propane conversion throughout, and smaller, more economical reactors. In addition, product selectivities are enhanced at higher space velocity since cracking reactions to give undesireable light products such as methane and/or ethane are minimized.

TABLE 2 shows the product selectivities obtained in the reactions of FIG. 1 wherein it is assumed that in the case of the mixed feed all of the added olefin is converted to $C_6{}^+$ hydrocarbons. The results of TABLE 2 indicate that olefin addition to the propane feed increases pentane selectivity, suppresses cracking of propane to methane and ethane, and enhances the rate of propane conversion by an order of magnitude. Product selectivities for each feed at 312° C., 6184 kPa, and 20% propane conversion over a ZSM-5 catalyst are as follows:

TABLE 2

| Feed | WHSV | $C_1$ | $C_2$ | $i$-$C_4$ | $n$-$C_4$ | $C_5{}^+$ | $C_6{}^+$ liquid |
|---|---|---|---|---|---|---|---|
| Propane | 0.1 | 6.4 | 11.0 | 30.1 | 39.3 | 10.9 | 2.4 |
| Propane/Propylene (90:10) | 2.0 | 0.0 | 0.4 | 25.4 | 34.5 | 23.8 | 15.8 |

FIG. 2 compares the amount of propane conversion as a function of temperature. The propane feed is diluted with 10 wt. % propene. The pressure is held constant at 6184 kPa (900 psig). At 230° C. (450° F.), the conversion of the mixed feed is limited to less than 20 wt. %, whereas at higher temperatures (e.g., 300° C. and above), the propane conversion increases to greater than 20 wt. %.

Product selectivity curves for a mixed hydrocarbon feed containing 90 wt. % propane and 10 wt. % propene are plotted in FIG. 3. The weight hourly space velocity (WHSV) of the feed is 0.8, and the pressure is held constant at 6184 kPa (900 psig). A maximum point for the production of normal and iso butanes occurs at about 312° C. (600° F.). At this temperature, there is also a minimum point in the graph corresponding to the amount of $C_6{}^+$ aliphatic and aromatic hydrocarbons in the product. The amount of cracked products, methane and ethane, in the overall product yield increases with increasing temperature.

FIG. 4 shows the relationship between the amount of propane reacted and the temperature of the reaction when the feed composition is 20 wt. % propane and 80 wt. % propene. Propane conversion decreases with increasing reaction temperature when the feed comprises about 80 wt. % mono-olefin. This effect is observed most dramatically in the case of lower space velocities, e.g., when the weight hourly space velocity (WHSV) of the olefin-rich feed (20 wt. % propane, 80 wt.% propene) is 0.1. In such a case, at temperatures of about 285° C. (550° F.) and higher, there is negative propane conversion, i.e., propane is actually produced by the reaction. TABLE 3 shows the product selectivities obtained in the reaction of FIG. 4 at 230° C. and 0.1 WHSV when it is assumed that all of the added olefin is converted to $C_6{}^+$ hydrocarbons.

TABLE 3

| % propane conversion | WHSV | $C_1$ | $C_2$ | $i$-$C_4$ | $n$-$C_4$ | $C_5{}^+$ |
|---|---|---|---|---|---|---|
| 43.4 | 0.1 | 0.0 | 0.0 | 29.6 | 12.1 | 58.2 |

FIG. 5 shows the comparison between the experimental results of propane conversion with a mixed feed and the equilibrium predictions. At propane mole fractions of 0.5 and less, there is a negative conversion of propane feed, propane being produced by the reaction. These results demonstrate the importance of propane/propylene feed ratio in controlling propane conversion. Propane conversion is highest when the propane/propylene feed ratio is greater than about 1.5:1.

FIG. 6 shows the optimum temperature range for the conversion of four different propane/propylene mixed feeds. For feedstocks comprising about 80 wt. % to 90 wt. % propane and about 10 wt. % to 20 wt. % propylene, the optimum temperature range for propane conversion is about 315° C. to 400° C.

In a general example, the invention is useful for upgrading a $C_3$ cut from an FCC off gas unit. The $C_3$ fraction, consisting essentially of about 40 wt. % propane and 60 wt. % propylene, is contacted under conversion conditions in a fixed bed reaction zone with a crystalline acidic metallosilicate catalyst for partial conversion of the propane to higher molecular weight hydrocarbons. Elluent from the reaction zone is recovered and subsequently fractionated into an isobutane stream, a $C_5{}^+$ hydrocarbon stream, a $C_2{}^-$ light gas stream, and a $C_3$-$C_4$ hydrocarbon stream. Propane is separated from the $C_3$-$C_4$ stream and recycled to the fixed bed reaction zone. This cycle stream is employed to maintain the mixed feed composition to about 60 wt. % to 90 wt. % propane.

The following Examples are included to illustrate the advantages of the present invention.

EXAMPLE 1

A liquid feed comprising propane is charged to a continuous tubular packed bed reactor containing about 11 g of crushed HZSM-5 catalyst. The catalyst has a silica:alumina ratio of 70 and an acid cracking (alpha) value of 194. The liquid propane is vaporized by heating means in a section above the catalyst bed. Gas and vapor products are analyzed with an on-line gas chromatograph. Liquid products are collected and analyzed off-line with a gas chromatograph. This is a comparative example and as such forms no part of the present invention. Results of the experiment are given in Table 4 below.

TABLE 4

|  | RUN 1 | | | | RUN 2 | | | |
|---|---|---|---|---|---|---|---|---|
| Time on Stream (hrs) | 8 | 25 | 31 | 19 | 25 | 42 | 48 | 66 |
| Temperature (°C.) | 312 | 312 | 312 | 312 | 367 | 367 | 367 | 367 |
| Pressure (kPa) | 2060 | 2060 | 6181 | 6181 | 6181 | 6181 | 2060 | 2060 |
| WHSV | 0.5 | 0.1 | 0.5 | 0.1 | 0.5 | 0.1 | 0.5 | 0.1 |
| % propane conv. | 4 | 12 | 5 | 19 | 43 | 57 | 33 | 44 |
| Product Yield (wt. %) | | | | | | | | |
| methane | 0.2 | 0.8 | 0.3 | 1.2 | 3.4 | 9.3 | 1.8 | 3.7 |
| ethane | 0.3 | 1.3 | 0.4 | 2.1 | 7.9 | 23.9 | 3.6 | 11.3 |
| propane | 96 | 88 | 95 | 81 | 57 | 43 | 67 | 56 |
| propene | 0 | 0 | 0 | 0 | 0.1 | 0 | 0 | 0 |
| isobutane | 1 | 4 | 2 | 6 | 9 | 58 | 8 | 7 |
| n-butane | 1 | 5 | 2 | 7 | 12 | 7 | 11 | 11 |
| $C_5$ | 0.3 | 1.0 | 0.5 | 2 | 7 | 4 | 5 | 6 |
| $C_6^+$ | 0.5 | 0.6 | 0.5 | 0.7 | 4 | 7 | 4 | 6 |
| Selectivity (wt. %) | | | | | | | | |
| methane | 5 | 7 | 5 | 6 | 8 | 16 | 5 | 8 |
| ethane | 7 | 11 | 9 | 11 | 18 | 42 | 11 | 26 |
| isobutane | 32 | 30 | 29 | 30 | 21 | 10 | 23 | 16 |
| n-butane | 36 | 41 | 39 | 39 | 28 | 13 | 33 | 24 |
| $C_5$ | 7 | 8 | 10 | 11 | 16 | 7 | 15 | 13 |
| $C_6^+$ | 13 | 5 | 9 | 4 | 9 | 12 | 13 | 13 |

EXAMPLE 2

A liquid feed comprising a mixture of propane (88 wt. %) and propylene (12 wt. %) is charged to a continuous tubular packed bed reactor containing about 11 g of the catalyst described in Example 1. The liquid mixed feed is vaporized by heating means in a section above the catalyst bed. Results of the experiment are given in Table 5 below.

TABLE 5

|  | RUN 1 | | RUN 2 | | RUN 3 | | RUN 4 | | |
|---|---|---|---|---|---|---|---|---|---|
| Time on Stream (hrs) | 17 | 23 | 7 | 7 | 25 | 31 | 6 | 24 | 29 |
| Temperature (°C.) | 312 | 312 | 312 | 312 | 312 | 312 | 230 | 230 | 367 |
| Pressure (kPa) | 6181 | 6181 | 6181 | 2060 | 2060 | 2060 | 6181 | 6181 | 6181 |
| WHSV | 0.1 | 0.5 | 0.8 | 0.8 | 0.1 | 0.5 | 0.8 | 0.1 | 0.8 |
| % propane conv. | 28 | 19 | 17 | 15 | 20 | 15 | 0.4 | 7 | 41 |
| Product Yield (wt. %) | | | | | | | | | |
| methane | 1.2 | 0.3 | 0.2 | 0.1 | 0.7 | 0.3 | 0 | 0 | 2 |
| ethane | 3 | 0.7 | 0.4 | 0.3 | 2 | 0.6 | 0 | 0 | 5 |
| propane | 63 | 72 | 73 | 75 | 70 | 75 | 88 | 82 | 52 |
| propene | 0 | 0.1 | 0.1 | 0 | 0 | 0 | 0 | 0.1 | 0 |
| isobutane | 10 | 8 | 7 | 7 | 10 | 7 | 2 | 3 | 10 |
| n-butane | 11 | 10 | 10 | 9 | 11 | 10 | 1 | 2 | 12 |
| $C_5$ | 7 | 4 | 4 | 4 | 5 | 4 | 2 | 3 | 7 |
| $C_6^+$ | 5 | 5 | 5 | 5 | 3 | 4 | 8 | 10 | 14 |
| Selectivity (wt. %) | | | | | | | | | |
| methane | 3.2 | 1.0 | 0.6 | 0.3 | 2.4 | 1 | 0 | 0 | 4 |
| ethane | 8 | 2.4 | 1.7 | 1.2 | 6.4 | 2.4 | 0 | 0 | 11 |
| isobutane | 28 | 27 | 27 | 27 | 32 | 29 | 13 | 15 | 19 |
| n-butane | 31 | 36 | 37 | 35 | 36 | 38 | 4 | 10 | 24 |
| $C_5$ | 18 | 15 | 16 | 18 | 15 | 15 | 16 | 17 | 14 |
| $C_6^+$ | 12 | 18 | 18 | 19 | 8 | 15 | 68 | 57 | 29 |

|  | RUN 5 | | | | | | | | | RUN 6 | | | |
|---|---|---|---|---|---|---|---|---|---|---|---|---|---|
| Time on Stream (hrs) | 5 | 24 | 29 | 48 | 53 | 72 | 77 | 96 | 102 | 7 | 25 | 31 | 49 |
| Temperature (°C.) | 367 | 367 | 367 | 422 | 422 | 422 | 312 | 312 | 312 | 312 | 312 | 422 | 422 |
| Pressure (kPa) | 6181 | 6181 | 6181 | 6181 | 6181 | 6181 | 6181 | 6181 | 6181 | 6181 | 6181 | 6181 | 6181 |
| WHSV | 0.5 | 0.1 | 0.2 | 0.2 | 0.8 | 0.1 | 0.8 | 0.2 | 0.8 | 0.5 | 0.11 | 0.25 | 0.1 |
| % propane conv. | 25 | 57 | 47 | 69 | 62 | 86 | 18 | 25 | 19 | 15 | 20 | 69 | 84 |
| Product Yield (wt. %) | | | | | | | | | | | | | |
| methane | 1.6 | 7 | 7 | 14 | 7 | 21 | 0.1 | 0.2 | 0 | 0.1 | 0.4 | 15 | 21 |
| ethane | 4 | 19 | 18 | 28 | 18 | 36 | 0.2 | 0.6 | 0.2 | 0.2 | 0.9 | 31 | 37 |
| propane | 66 | 38 | 47 | 28 | 38 | 14 | 74 | 69 | 72 | 75 | 71 | 27 | 14 |
| propene | 1.3 | 0 | 0 | 0 | 0.1 | 0 | 0 | 0.1 | 0.1 | 0 | 0 | 0 | 0.1 |
| isobutane | 7 | 5 | 7 | 3 | 4 | 1 | 5 | 7 | 5 | 6 | 8 | 3 | 1 |
| n-butane | 7 | 6 | 8 | 5 | 6 | 1.5 | 7 | 9 | 7 | 8 | 10 | 4 | 2 |
| $C_5$ | 5 | 4 | 4 | 3 | 4 | 1 | 5 | 4 | 5 | 5 | 4 | 2 | 1 |
| $C_6^+$ | 8 | 21 | 8 | 20 | 28 | 27 | 11 | 12 | 12 | 6 | 6 | 19 | 24 |
| Selectivity (wt. %) | | | | | | | | | | | | | |
| methane | 5 | 11 | 14 | 19 | 11 | 24 | 0.2 | 0.6 | 0.2 | 0.3 | 1.3 | 20 | 24 |
| ethane | 13 | 31 | 34 | 38 | 27 | 41 | 0.8 | 1.6 | 0.6 | 1 | 3 | 42 | 43 |
| isobutane | 20 | 8 | 13 | 5 | 6 | 1 | 18 | 22 | 17 | 23 | 28 | 4 | 2 |
| n-butane | 22 | 10 | 16 | 6 | 9 | 2 | 25 | 28 | 24 | 33* | 33 | 5 | 2 |
| $C_5$ | 16 | 6 | 8 | 4 | 5 | 1 | 18 | 13 | 18 | 20 | 15 | 3 | 1 |
| $C_6^+$ | 24 | 34 | 16 | 28 | 41 | 31 | 39 | 36 | 41 | 23 | 21 | 26 | 28 |

EXAMPLE 3

A liquid feed comprising a mixture of propane (78 wt. %) and propylene (22 wt. %) is charged to a continuous tubular packed bed reactor containing about 11 g of the catalyst described in Example 1. The liquid mixed feed is vaporized by heating means in a section above the catalyst bed. Results of the experiment are given in Table 6 below.

TABLE 6

|  | RUN 1 | RUN 2 | | | | | | |
|---|---|---|---|---|---|---|---|---|
| Time on Stream (hrs) | 7 | 7 | 25 | 31 | 49 | 55 | 73 | 79 |
| Temperature (°C.) | 24 | 312 | 312 | 312 | 367 | 367 | 367 | 422 |
| Pressure (kPa) | 6181 | 6181 | 6181 | 6181 | 6181 | 6181 | 6181 | 6181 |
| WHSV | 0.2 | 0.8 | 0.1 | 0.2 | 0.2 | 0.8 | 0.2 | 0.8 |
| % propane conv. | −1.7 | 25 | 27 | 29 | 42 | 36 | 42 | 59 |
| Product Yield (wt. %) | | | | | | | | |
| methane | 0 | 0.1 | 0.9 | 0.6 | 5 | 1 | 5 | 8 |
| ethane | 0 | 0.4 | 3 | 2 | 15 | 4 | 13 | 21 |
| propane | 81 | 60 | 59 | 57 | 46 | 51 | 47 | 33 |
| propene | 12 | 0.1 | 0 | 0.1 | 0 | 0.1 | 0 | 0.1 |
| isobutane | 0.7 | 9 | 10 | 11 | 7 | 9 | 7 | 4 |
| n-butane | 0 | 12 | 11 | 12 | 8 | 12 | 9 | 6 |
| $C_5$ | 0 | 6 | 7 | 7 | 5 | 7 | 5 | 3 |
| $C_6^+$ | 6 | 13 | 11 | 11 | 14 | 17 | 15 | 26 |
| Selectivity (wt. %) | | | | | | | | |
| methane | 0 | 0.3 | 2.2 | 1.3 | 10 | 2.5 | 9 | 12 |
| ethane | 0.5 | 1 | 6 | 4 | 28 | 7 | 24 | 31 |
| isobutane | 11 | 23 | 23 | 25 | 13 | 18 | 14 | 6 |
| n-butane | 0 | 29 | 25 | 29 | 15 | 24 | 17 | 8 |
| $C_5$ | 0.6 | 15 | 16 | 16 | 8 | 13 | 9 | 5 |
| $C_6^+$ | 88 | 32 | 27 | 25 | 25 | 34 | 28 | 39 |

EXAMPLE 4

A liquid feed consisting essentially of a mixture of propane (20 wt. %) and propylene (80 wt. %) is charged to a continuous tubular packed bed reactor containing about 11 g of the catalyst described in Example 1. The liquid mixed feed is vaporized by heating means in a section above the catalyst bed. Results of the experiment are given in Table 7.

TABLE 7

|  | RUN 1 | | | | | | | RUN 2 | |
|---|---|---|---|---|---|---|---|---|---|
| Time on Stream (hrs) | 6 | 24 | 29 | 48 | 53 | 72 | 77 | 7 | 25 |
| Temperature (°C.) | 202 | 230 | 230 | 257 | 257 | 312 | 312 | 257 | 257 |
| Pressure (kPa) | 6181 | 6181 | 6181 | 6181 | 6181 | 6181 | 6181 | 2060 | 2060 |
| WHSV | 0.8 | 0.1 | 0.8 | 0.1 | 0.8 | 0.1 | 0.8 | 0.8 | 0.1 |
| % propane conv. | 14 | 47 | 28 | 22 | 33 | −53 | 22 | 27 | −19 |
| Product Yield (wt. %) | | | | | | | | | |
| methane | 0 | 0 | 0 | 0 | 0 | 0.3 | 0 | 0 | 0 |
| ethane | 0 | 0 | 0 | 0.1 | 0 | 1.1 | 0.1 | 0 | 0 |
| propane | 17 | 11 | 14 | 16 | 13 | 31 | 16 | 15 | 24 |
| propene | 0 | 0 | 0 | 0.6 | 1.0 | 0.9 | 2 | 0.7 | 1.5 |
| isobutane | 1 | 3 | 1 | 7 | 2 | 10 | 7 | 1 | 5 |
| n-butane | 0.3 | 1.1 | 0.4 | 5 | 0.3 | 9 | 4 | 0.4 | 1.2 |
| $C_5$ | 2 | 4 | 2 | 9 | 4 | 9 | 11 | 3 | 7 |
| $C_6^+$ | 79 | 81 | 82 | 64 | 80 | 38 | 60 | 80 | 62 |
| Selectivity (wt. %) | | | | | | | | | |
| methane | 0 | 0 | 0 | 0 | 0 | 0.4 | 0 | 0 | 0 |
| ethane | 0 | 0 | 0 | 0.1 | 0 | 1.6 | 0.1 | 0 | 0.1 |
| isobutane | 2 | 3 | 1 | 8 | 2 | 15 | 9 | 2 | 7 |
| n-butane | 0.4 | 1 | 0.4 | 6 | 0.4 | 13 | 4 | 0.5 | 2 |
| $C_5$ | 2 | 5 | 2 | 11 | 4 | 14 | 14 | 3 | 9 |
| $C_6^+$ | 96 | 91 | 96 | 76 | 94 | 56 | 73 | 95 | 83 |

EXAMPLE 5

The catalyst described in Example 1 is impregnated with an aqueous solution containing platinum, and then calcined in air. The platinum content of the sample is about 0.4 weight percent. About 5 g of crushed Pt-HZSM-5 catalyst pellets are loaded into a continuous packed bed reactor and reduced in flowing hydrogen at 400° C. for 16 hours. The temperature is then reduced to 260° C., the hydrogen flow stopped, and the liquid mixture comprising propane (80 wt % and propylene (20 wt %) is charged to the reactor. The liquid mixed feed is vaporized by heating means in a section above the catalyst bed. Results of the experiment are given in Table 8.

TABLE 8

|  | RUN 1 | | |
|---|---|---|---|
| Time on Stream (hrs) | 7 | 31 | 55 |
| Temperature (°C.) | 260 | 260 | 260 |
| Pressure (kPa) | 6181 | 6181 | 6181 |
| WHSV | 1.0 | 0.5 | 1.8 |
| % propane conv. | 17 | 19 | 8 |
| Product Yield (wt. %) | | | |
| methane | 0 | 0 | 0 |
| ethane | 0.1 | 0.1 | 01 |
| propane | 64.4 | 63.3 | 71.8 |
| propene | 0.1 | 0.1 | 0.1 |
| isobutane | 1.4 | 1.5 | 0.9 |
| n-butane | 0.8 | 0.9 | 0.3 |
| $C_5$ | 3.0 | 3.2 | 1.7 |
| $C_6^+$ | 30.2 | 30.9 | 25.2 |
| Selectivity (wt. %) | | | |
| methane | 0 | 0 | 0 |
| ethane | 0.2 | 0.2 | 0.2 |
| isobutane | 3.9 | 4.1 | 3.2 |
| n-butane | 2.3 | 2.6 | 0.9 |
| $C_5$ | 8.4 | 8.6 | 6.0 |
| $C_6^+$ | 85.1 | 84.5 | 89.7 |

The examples above demonstrate the improvement in the conversion of propane to valuable hydrocarbons over a ZSM-5 type catalyst when a minor amount of olefin is added to the propane feed. Beneficial results, such as an increase in the production of isobutane, are obtained with a minimum cost to the petroleum refiner.

While the invention has been described in reference to certain embodiments, there is no intent to limit the inventive concept except as set forth in the following claims.

We claim:

1. A process for converting $C_3$ aliphatic hydrocarbon feed to produce primarily $C_4^+$ aliphatic hydrocarbons comprising contacting a $C_3$ feed containing propane and about 10% to 40% by weight mono-olefin with an acidic shape selective medium pore zeolite catalyst having a Constraint Index of 1 to 12 at a temperature of about 200° to 400° C. and a pressure above about 3400 kPa under reaction conditions to convert at least 10% of the propane; and recovering a product rich in $C_4+$ aliphatic hydrocarbons and not more than 10 wt. % total methane and ethane.

2. A process for preparing a hydrocarbon mixture comprising primarily $C_4+$ aliphatic hydrocarbons while minimizing the formation of methane and ethane, the process consisting essentially of:

contacting in a fixed bed reaction zone under conversion conditions a mixed feed comprising about 60 wt. % to 90 wt. % propane and a mono-olefin or olefin precursor with a porous crystalline acidic metallosilicate zeolite catalyst having an acid cracking activity (alpha value) greater than 100, to convert at least 10% of the propane; and withdrawing from the reaction zone a hydrocarbon product containing no more than 10 wt. % cracking products consisting of methane and ethane.

3. A process according to claim 2 wherein the conversion conditions comprise a temperature of about 200° C. to 370° C., a pressure above about 3400 kPa, a weight hourly space velocity of about 0.1 to 100, and in the essential absence of hydrogen.

4. A process according to claim 2 wherein unconverted propane is separated from the hydrocarbon product and recycled to the fixed bed reaction zone.

5. A process according to claim 2 wherein the catalyst comprises aluminosilicate H-ZSM-5 zeolite free of hydrogenation-dehydrogenation components.

6. A process according to claim 2 wherein the olefin comprises propylene.

7. A process according to claim 2 wherein the mixed feed comprises about 80 wt. % propane and 20 wt. % propylene.

8. In a process for the production of n-butane, isobutane, and primarily $C_5+$ aliphatic hydrocarbons by contacting a propane feed in the essential absence of added hydrogen and at a pressure of at least about 3400 kPa with a catalyst comprising a crystalline zeolite having a silica-to-alumina ratio of at least 12 and a Constraint Index of 1 to 12 under a combination of conditions of temperature, pressure, and WHSV effective to convert up to about 25% by weight of the propane feed, the improvement comprising:

adding to the propane feed from about 10% to 20% by weight of at least one $C_2-C_{16}$ mono-olefin, thereby increasing the reaction rate of the propane feed; and obtaining a product comprising butanes and no more than 10% by weight total methane and ethane.

9. A process according to claim 8 wherein the mono-olefin is a $C_2-C_4$ hydrocarbon and the product contains at least 10 wt. % $C_5+$ aliphatic hydrocarbons, based on conversion of the propane alone.

10. A process according to claim 8 wherein the product contains no more than 40 wt. % aromatics.

11. A process according to claim 8 wherein the product is fractionated to obtain isobutane, a hydrocarbon stream consisting essentially of unreacted propane, a $C_2-$ hydrocarbon stream, and a $C_5+$ hydrocarbon stream.

12. A process according to claim 11 wherein the stream consisting essentially of unreacted propane is recycled for contact with the crystalline zeolite catalyst.

13. A process for preparing a hydrocarbon mixture comprising $C_4+$ aliphatic hydrocarbons while minimizing the formation of methane and ethane, the process consisting essentially of:

contacting in a fixed bed reaction zone under conversion conditions a mixed feed comprising propane and a mono-olefin or olefin precursor with a porous crystalline acidic metallosilicate zeolite catalyst having a Constraint Index of 1 to 12 and having an alpha value greater than 100, to convert at least 10 wt. % of the propane;

withdrawing from the reaction zone a hydrocarbon product containing not more than 10 wt. % cracking products consisting of methane and ethane; and separating a hydrocarbon stream containing unreacted propane from the hydrocarbon product; and recycling the stream to be fixed bed reaction zone in an amount sufficient to maintain the mixed feed composition at about 60 wt. % to 90 wt. % propane.

14. A process according to claim 13 wherein the fixed bed reaction zone is maintained at a temperature of about 200° C. to 400° C. and a pressure of above about 3400 kPa.

15. A process according to claim 13 wherein the zeolite catalyst comprises a crystalline metallosilicate having the structure of ZSM-5.

16. A process according to claim 13 wherein the hydrocarbon product is further separated to obtain isobutane, a $C_2-$ hydrocarbon stream, and a $C_5+$ hydrocarbon stream.

17. A process for catalytic conversion of an olefin-rich hydrocarbon feedstream containing propane comprising contacting the feedstream with an acid medium pore zeolite catalyst in a catalytic reaction zone to obtain a product containing $C_4+$ aliphatic hydrocarbons;

separating the product to obtain a first fraction rich in unreacted propane and a second fraction comprising $C_4+$ aliphatic hydrocarbons;

recycling the propane-rich first fraction for admixture with the olefin-rich hydrocarbon feedstream to obtain a composite feedstream comprising about 60–90 wt. % propane and about 10–40 wt. % olefin; and conducting the composite feedstream to the reaction zone for catalytic conversion.

18. A process according to claim 17 wherein the catalytic reaction zone is operated at a temperature of about 200° C. to 400° C. and the conversion reaction is conducted in the essential absence of added hydrogen.

19. A process according to claim 17 wherein the catalytic reaction zone contains an amount of acidic zeolite catalyst having the structure of ZSM-5 and effective to convert the composite feedstream to higher hydrocarbon products.

20. A process according to claim 17 wherein the catalytic reaction zone is operated at a pressure above about 3400 kPa.

21. A process according to claim 17 wherein the composite feedstream is catalytically converted to a hydrocarbon product containing at least 50 wt. % butanes and not more than 10 wt. % methane and ethane, based on conversion of propane alone.

22. A process according to claim 17 wherein at least 10 wt. % of the propane in the composite feedstream is converted to product.

23. A process according to claim 8 wherein the WHSV is about 0.1 to 100 and the temperature is below about 370° C.

* * * * *